United States Patent [19]

Rüger et al.

[11] Patent Number: 6,030,744
[45] Date of Patent: Feb. 29, 2000

[54] SILVER-HALIDE RECORDING MATERIAL WITH IMPROVED STORAGE STABILITY TO PRODUCE NEGATIVES WITH ULTRAHARD-GRADATION CONTRAST

[75] Inventors: Reinhold Rüger, Rödermark; François Varescon, Neu-Isenburg, both of Germany

[73] Assignee: Agfa-Gevaert NV, Germany

[21] Appl. No.: 09/180,043

[22] PCT Filed: May 7, 1997

[86] PCT No.: PCT/EP97/02333

§ 371 Date: Oct. 29, 1998

§ 102(e) Date: Oct. 29, 1998

[87] PCT Pub. No.: WO97/42546

PCT Pub. Date: Nov. 13, 1997

[30] Foreign Application Priority Data

May 7, 1996 [DE] Germany ............................ 196 18 196

[51] Int. Cl.[7] .............................. G03C 1/295; G03C 1/10
[52] U.S. Cl. .......................... 430/264; 430/600; 430/603; 430/608
[58] Field of Search ...................................... 430/503, 264, 430/600, 603, 440, 608

[56] References Cited

U.S. PATENT DOCUMENTS

| 5,104,784 | 4/1992 | Shuto et al. | 430/567 |
| 5,372,921 | 12/1994 | Gingello et al. | 430/264 |
| 5,663,034 | 9/1997 | Ruger | 430/264 |
| 5,935,769 | 8/1999 | Tsukada | 430/440 |

FOREIGN PATENT DOCUMENTS

| 393 477 | 10/1990 | European Pat. Off. |
| 800 109 | 8/1997 | European Pat. Off. |

*Primary Examiner*—Richard L. Schilling
*Assistant Examiner*—Amanda C. Walke
*Attorney, Agent, or Firm*—Connolly Bove Lodge & Hutz LLP

[57] ABSTRACT

Photographic silver-halide materials for producing negatives with ultrahard-gradation gamma contrast, which contain a hydrazine compound and a contrast-boosting amino compound and/or phosphonium compound, demonstrate an undesirable increase in fog during storage. By adding a sulphite salt to the emulsion, storage-stable materials are obtained in which sensitivity and contrast are increased. The invention can be used to produce images during reproduction in the pre-printing stage.

14 Claims, No Drawings

SILVER-HALIDE RECORDING MATERIAL WITH IMPROVED STORAGE STABILITY TO PRODUCE NEGATIVES WITH ULTRAHARD-GRADATION CONTRAST

The invention relates to a photographic silver halide recording material for producing black and white negatives with ultrahard-gradation contrast which contains a hydrazine compound and a contrast-boosting amino compound.

During photomechanical reproduction, halftone images frequently have to be converted into raster images. This is achieved using silver halide materials which are developed by special processes to ultrahard-gradation contrast, i.e. to a maximum gradation of the characteristic curve higher than 10. Known processes include, for example, the lithographic process employing low-sulphite, formaldehyde-containing hydroquinone developers. Development in the presence of hydrazine compounds has been widely practised in recent times.

With this process, certain amino compounds are frequently used further to boost the contrast. For example, EP-00 32 456-B1 claims a process in which a recording material is processed in the presence of a hydrazine compound with a hydroquinone-3-pyrazolidinone developer containing a contrast-boosting quantity of an amino compound. However, these developers have a number of drawbacks. For some years, therefore, contrast-boosting amino compounds have also been incorporated into the photographic recording material together with hydrazine compounds.

German Offenlegungsschrift DE-A-43 10 327 describes a process for producing negatives with ultrahard-gradation contrast, in which the silver halide recording material is developed in the presence of compounds of which the molecules contain at least one quaternary nitrogen atom and at least one tertiary amine function.

EP-04 73 342-A1 describes a photographic silver halide material which may be developed to ultrahard-gradation contrast in a developer with a pH<11. The light-sensitive coating of this material contains a hydrazine compound having a specific formula as well as an amino or a quaternary onium compound and is adjusted to a pH of at least 5.9.

U.S. Pat. No. 4, 975,354 proposes that certain secondary or tertiary amino compounds also containing at least three oxyethylene units in their molecule be incorporated into the silver halide materials as contrast booster in addition to hydrazine compounds.

EP 04 22 677 describes the use of tertiary amino compounds with at least three oxyethylene units in the molecule as development accelerators in developer solutions which also act in the presence of hydrazine compounds.

EP 05 39 998 claims silver halide materials which contain thioether compounds with a tertiary amino group in addition to hydrazine compounds.

Further amino compounds which have a contrast-boosting effect when incorporated with hydrazine compounds are described in EP-A-06 63 611.

Finally, it is also known from U.S. Pat. No. 4,929,535 that certain phosphonium compounds may display a contrast-boosting effect in hydrazine compound-containing silver halide materials.

A drawback frequently observed in known high-contrast recording materials is a pronounced change in the photographic properties during prolonged storage.

The fog increases in particular. The normal precautions against fog, namely the addition of anti-fogging agents to the emulsion and less intensive chemical ripening have resulted in inadequate speed. Furthermore, the normal anti-fogging agents such as benzotriazoles, nitroindazoles and mercaptotetrazoles inhibit infectious development, resulting in unsatisfactory contrast, particularly in the case of high-speed processing which is normal nowadays.

The object of the invention is to propose a silver halide recording material which is suitable for producing negatives with ultrahard-gradation contrast and a short processing time, which has high speed with reduced fog, and of which the photographic properties, in particular the fog and contrast do not deteriorate during storage.

These objects are achieved with a silver halide recording material according to the main claim.

It has in fact surprisingly been found that a photographic silver halide material comprising at least one light-sensitive silver halide emulsion layer on a substrate, the silver halide emulsion layer or a layer in a reactive relationship therewith containing a hydrazine compound and a contrast-boosting amino compound and/or phosphonium compound, has excellent stability in storage if the silver halide emulsion layer or a layer in a reactive relationship therewith contains a sulphite, hydrogen sulphite or bisulphite salt.

The sulphite, hydrogen sulphite or bisulphite salt is preferably an alkali metal salt, in particular a lithium, sodium or potassium salt. Examples of suitable salts include $Na_2SO_3$, $NaHSO_3$, $Li_2S_2O_5$, $K_2SO_3$, $KHSO_3$, $K_2S_2O_5$; $CaSO_3$ and $MgHSO_3$, for example, may also be used.

The sulphite, hydrogen sulphite or bisulphite salt may be added to the emulsion at any time during the production process. The addition is preferably made after removal of the soluble salts; particularly preferably on completion of chemical ripening. The salt may be added in solid form or as a—preferably aqueous— solution. It is also possible to treat the emulsion layer of the recording material with a solution of the salt after application to the substrate and drying.

The quantity of sulphite, hydrogen sulphite or bisulphite contained in the emulsion may be varied in wide limits, depending upon the requirements. It preferably corresponds to 0.05 to 20 millimoles of sulphite ions per mole of silver halide. A particularly preferred range lies between 0.1 and 10 millimoles of sulphite ions per moles of silver halide. One mole of a sulphite or hydrogen sulphite salt corresponds in each case to one mole of sulphite ions, but one mole of a bisulphite salt to two moles of sulphite ions.

The hydrazine compound contained in the recording material according to the invention may be incorporated into either one or several layers of the recording material in a known manner. These may be layers which contain the light-sensitive silver halide as well as layers which are in a reactive relationship with the aforementioned layers, i.e. are so arranged that substances are able to diffuse from one layer to the other if a concentration gradient is maintained by reactions. Solutions as well as dispersions of the hydrazine compound may be added to the coating solutions to assist incorporation.

Suitable hydrazine compounds are described, for example, in Research Disclosure 235 010 (November 1983), DE-27 25 743-A1, EP-00 32 456-B1, EP-01 26 000-A2, EP-01 38 200-A2, EP-02 03 521-A2, EP-02 17 310-A2, EP-02 53 665-A2, EP-03 24 391-A2, EP-03 24 426-A2, EP-03 26 443-A2, EP-03 56 898-A2, EP-04 73 342-A1, EP-05 01 546-A1, EP-04 81 565-A, EP-05 98 315-A1, EP-04 44 506-A.

Preferred hydrazine compounds are described by the general formula (H)

B represents a ballast group, G an activating group and L one of the groups —CO— and —CO—CO—. "Phenyl" represents a phenylene ring to which B and the hydrazine group are bound, preferably in the para-position, and which may be further substituted.

Preferred ballast groups include those which do not attract electrons, for example straight or branched alkyl groups, (for example methyl, ethyl, n-propyl, isopropyl, n-butyl, isobutyl, n-hexyl, n-octyl, t-octyl, n-decyl, n-dodecyl and similar groups), also alkoxy groups which contain one of the aforementioned alkyl groups as alkyl, as well as acylamino groups such as acetylamino, propanoylamino, butanoylamino, octanoylamino, benzoylamino, alkyl and arylsulphonamido and similar groups.

The above-mentioned groups may in turn be substituted with conventional photographic ballast groups as known from incorporated diffusion-resistant couplers and other immobilised photographic additives. These ballast groups typically contain at least 8 carbon atoms and may be selected from relatively inert aliphatic or aromatic groups, for example alkyl, alkoxy, phenyl, alkylphenyl, phenoxy, alkylphenoxy, arylacyl, arylamindo, alkylpyridinium-1-ylamido and similar groups.

The alkyl and alkoxy groups, including any ballast groups, preferably contain 1 to 20 carbon atoms and the acylamino groups preferably 2 to 21 carbon atoms.

However, these groups may contain up to 30 or more carbon atoms. Methoxyphenyl, tolyl, ballasted butyramidophenyl, butylsulphonamido and toluylsulphonamido are particularly preferred.

The preferred hydrazine compounds include those whose ballast group additionally contains an adsorption-promoting group. These groups promote the adsorption of the molecule on the surface of the silver halide crystals and are known per se. They typically contain at least one sulphur or nitrogen atom which is capable of forming a silver complex or otherwise has affinity for the silver halide surface. Preferred examples include thiourea, thiuronium, heterocyclic thioamide and triazole groups.

G is preferably hydrogen, optionally substituted alkyl (for example methyl, hydroxymethyl, monofluoromethyl, pyridinomethyl, phenoxymethyl, alkoxymethyl such as methoxymethyl), optionally substituted aralkyl (for example benzyl, o-hydroxybenzyl) and optionally substituted aryl (for example phenyl, 3,5-dichlorophenyl, o-methanesulphonamidophenyl, 4-methanesulphonylmethyl, 2-hydroxymethylphenyl), alkyl groups containing electron-attracting substituents, for example cationic groups with a quaternary nitrogen atom such as pyridinium and imidazolium, being particularly preferred.

G may also be further substituted, for example by alkyl, aralkyl, alkenyl, alkinyl, alkoxy, aryl, substituted amino, ureido, urethane, aryloxy, sulphamoyl, carbamoyl, alkyl or arylthio, alkyl or arylsulphonyl, alkyl or arylsulphinyl, hydroxy, halogen, cyan, sulpho, aryloxycarbonyl, acyl, alkoxycarbonyl, acyloxy, carbamide, sulphonamide, carboxyl, phosphamide, diacylamino, imide.

G may also be selected such that the L—G part of the molecule is separated with ring formation, as described, for example, in EP-B-02 53 665.

Examples of suitable hydrazine compounds include:

H-1

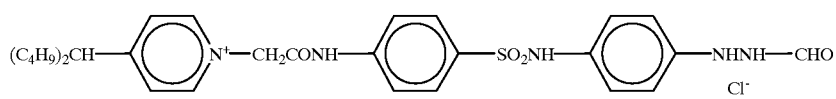

H-2

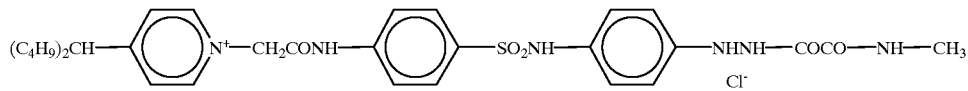

H-3

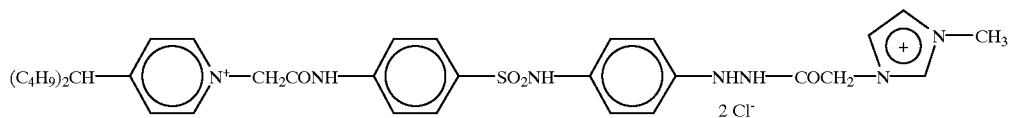

H-4

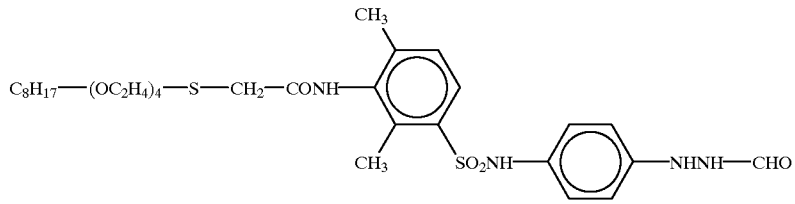

H-5
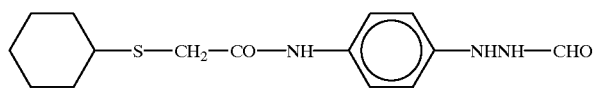
H-6
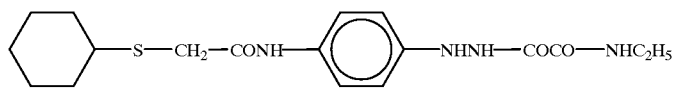
H-7
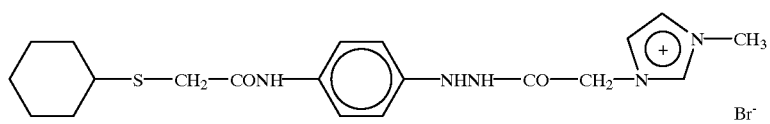
H-8
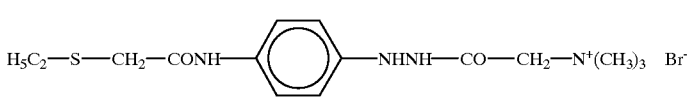
H-9
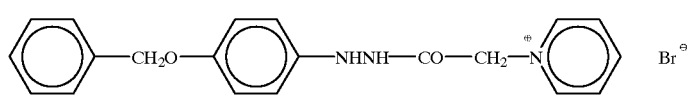
H-10
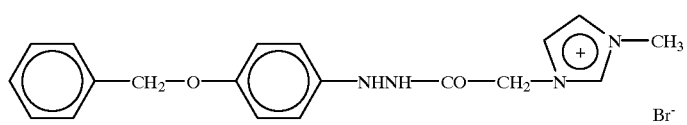
H-11
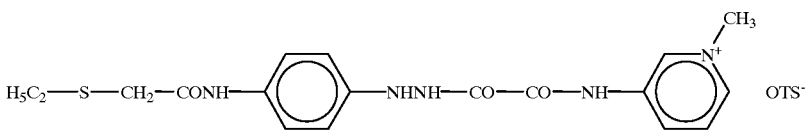
H-12
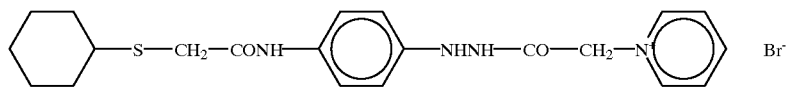
H-13
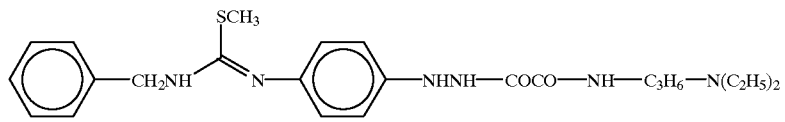
H-14
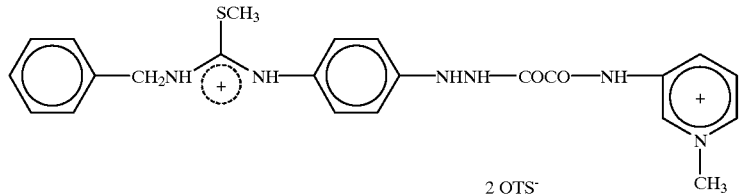
H-15
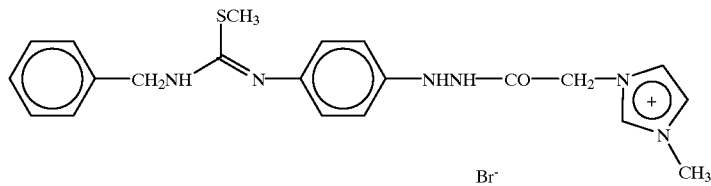

-continued

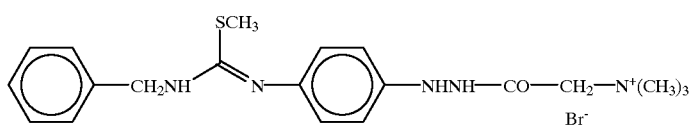

H-16

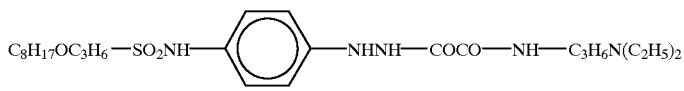

H-17

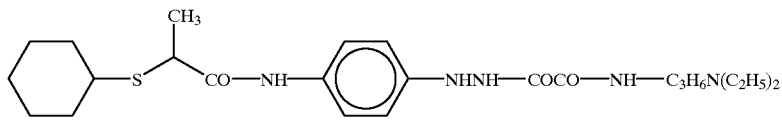

H-18

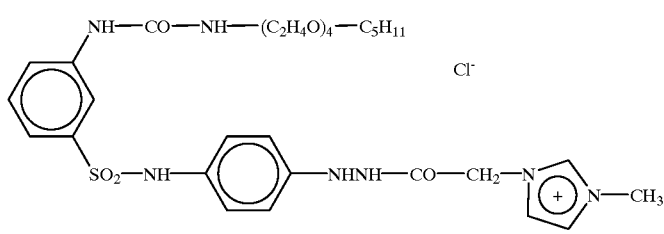

H-19

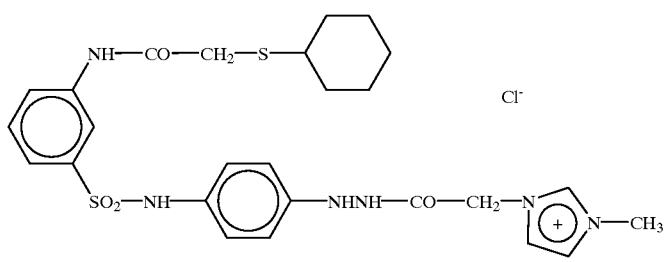

H-20

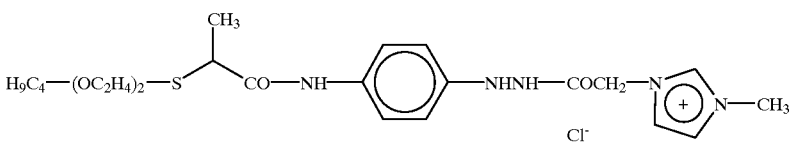

H-21

The quantity of hydrazine compound is preferably between $10^{-6}$ and $10^{-2}$ moles per mole of silver halide.

Suitable contrast-boosting amino compounds are known, for example, from U.S. Pat. No. 4,914,003, EP-A-06 18 491 and EP-A-06 63 611.

Amino compounds corresponding to general formula (A) are particularly preferred.

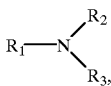

(A)

wherein each of the substituents $R_1$, $R_2$ and $R_3$ may be a hydrogen atom, an alkyl group, a substituted alkyl group, an alkenyl group, a substituted alkenyl group, an alkinyl group, an aryl group or a substituted aryl group, but the three are not all simultaneously hydrogen. The substituents may also be linked to one another to form one or two rings and may in turn be substituted by diffusion-inhibiting (ballast) groups and/or groups which promote adsorption with respect to silver halide surfaces.

Preferred amino compounds contain, in their molecule, at least one secondary or tertiary amino group and additionally a group with a quaternary nitrogen atom, a polyoxyalkylene chain, a thioether or thioketone group, a nitrile group, a sulphonyl urea or urethane group or a guanidine group.

In a particularly preferred embodiment of the invention, the contrast-boosting amino compound falls under one of general formulae (B), (C),or (D):

$$RR^1N-X-(CN)_n \qquad (B)$$

$$NC-X-NR^2-B-NR^2-X-CN \qquad (C)$$

$$RR^1N-X-N(CH_2CN)_2 \qquad (D)$$

The radicals R and $R^1$, which may be the same or different, each represent a straight-chained or branched alkyl group containing 1 to 6 carbon atoms, for example methyl, ethyl, n-propyl, isopropyl, n-butyl, isobutyl, n-hexyl. While including the nitrogen atom and optionally a further nitrogen atom, an oxygen atom or a carbonyl group, they may also form a heterocyclic ring with 5 to 12 members, for example a piperidine, pyrrolidine, pyrroline, oxazolidine, imidazoline, morpholine, pyrazane, azepine, oxazepine or azacyclodecane ring. Each of the groups R and $R^1$ may also be a benzyl group. The groups R and $R^1$ and also the heterocyclic rings corresponding to these groups may be further substituted, preferably with hydroxyl, alkoxy, alkylthio or alkylarnino groups, wherein the alkyl may contain 1 to 6 carbon atoms. Examples of these substituents include methoxy, ethoxy, propoxy, butoxy, ethylamino, dimethylamino, butylthio.

R or $R^1$ with their free end may also link with the combining group X to form a ring which includes the nitrogen atom of the tertiary amino group. A ring of this type may be, for example, a piperidine ring or a morpholine ring.

The divalent groups X and B to be combined are preferably straight-chained, branched or cyclic alkylene groups containing 1 to 20 carbon atoms, phenylene or aralkylene groups containing 7 to 20 carbons atoms or divalent chains consisting of 1 to 20 methylene groups in which oxygen, sulphur, amino groups, alkene or alkine groups or also polyoxyalkylene groups, in particular polyoxyethylene or polyoxypropylene groups containing 1 to 50 oxyalkyl units may additionally be incorporated. An ethylene or propylene group is particularly preferred. The above-mentioned groups may also be further substituted, for example with alkyl, hydroxyl and further tertiary amino groups.

The combining group X may also be trivalent and thus combine the tertiary amino group with two nitrilo groups. The groups mentioned in the foregoing paragraph are suitable if they comprise a further free valency instead of a hydrogen atom.

Examples include:

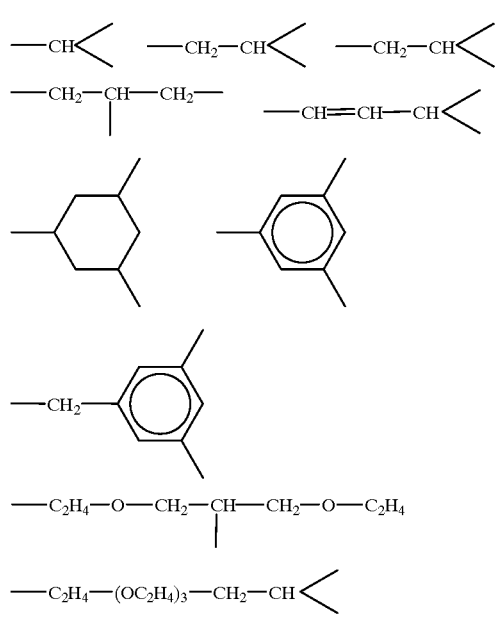

The radical $R^2$ in general formula (C) represents a saturated or unsaturated alkyl group, preferably containing 1 to 12 carbon atoms, an aryl group, preferably containing 6 to 14 carbon atoms or an aralkyl group, preferably containing 7 to 15 carbon atoms. These groups may in turn be substituted, for example with hydroxyl, amino, alkylamino and alkoxy groups, the alkyl preferably containing 1 to 6 carbon atoms. If an alkyl group is involved, it may also be bound by its end remote from the nitrogen to a carbon atom from group B to form a ring. A ring of this type may be, for example, a piperidine, pyrrolidine or hexahydroazepine ring. The two radicals $R^2$ may also form, together with B or with parts of B and with the two nitrogen atoms, one or two saturated rings, preferably with 5 or 6 members, for example pyrrolidine or piperidine rings.

Examples of suitable amino compounds include:

A-1

A-2

A-3

A-4

A-5
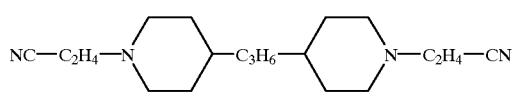

A-6

A-7

A-8

A-9
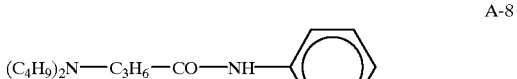

A-10
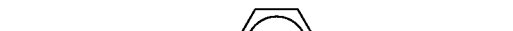

A-11
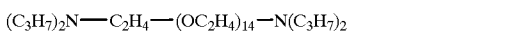

A-12
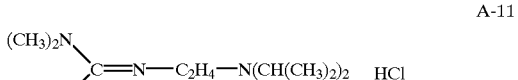

A-13
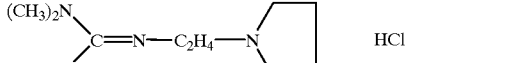

A-14
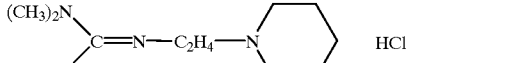

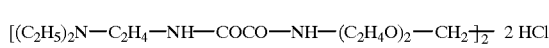

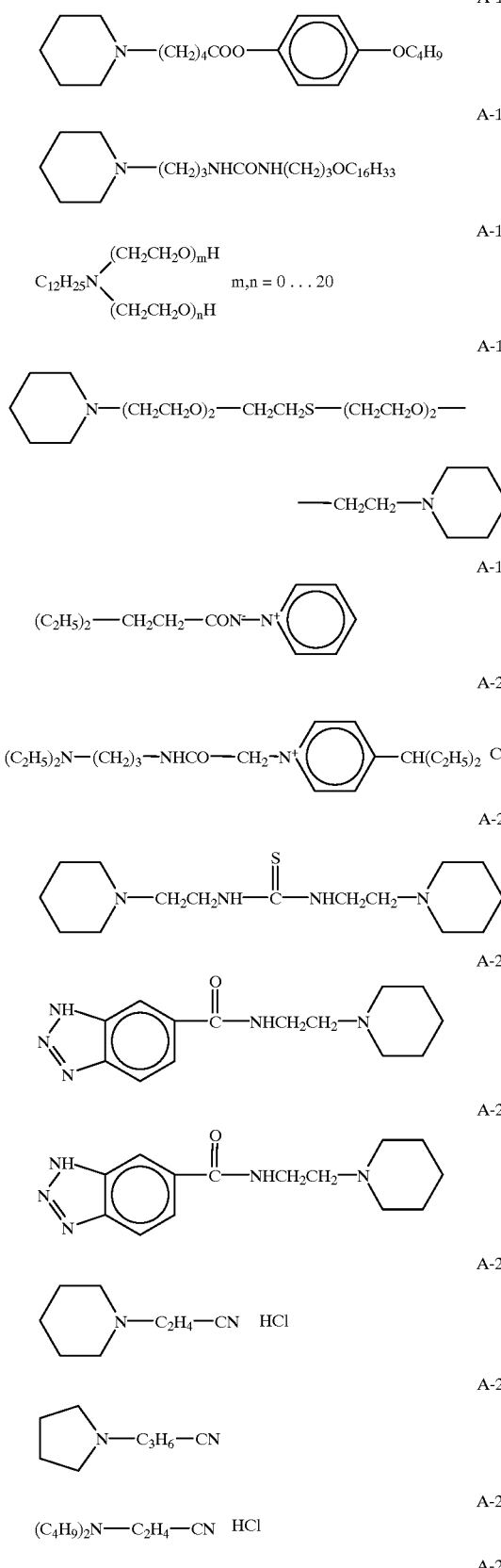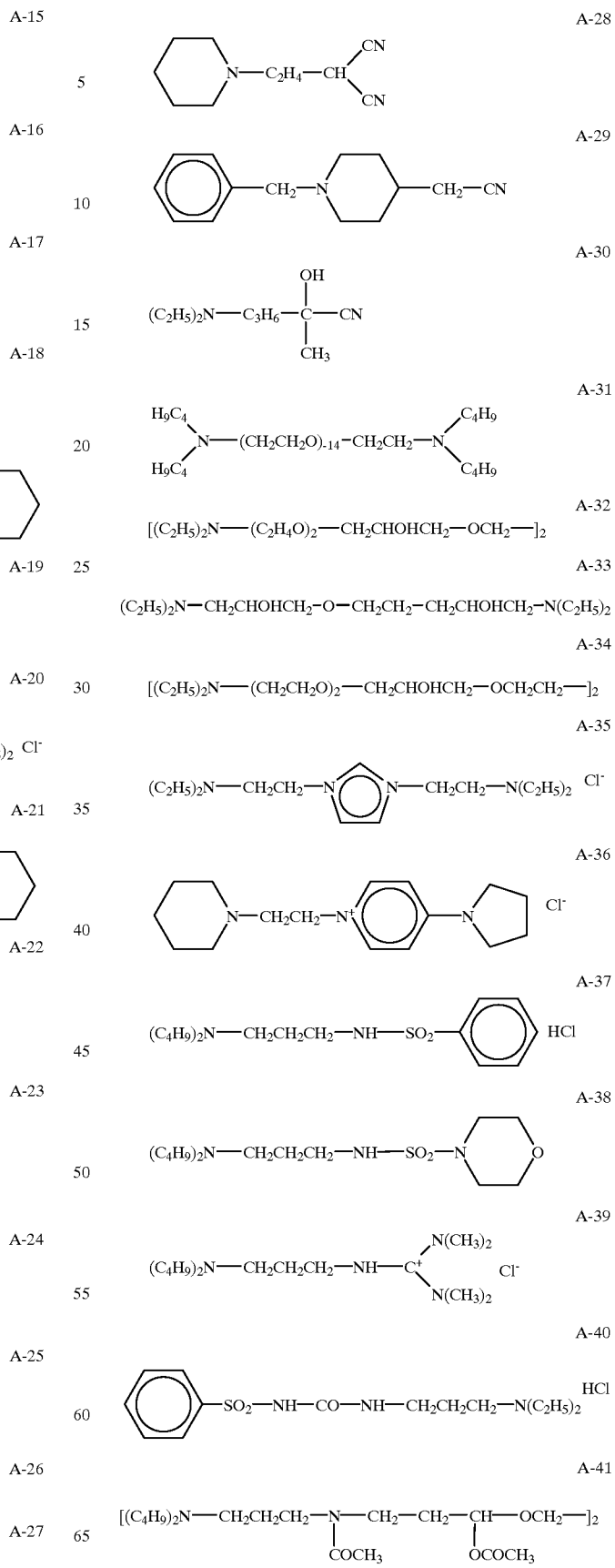

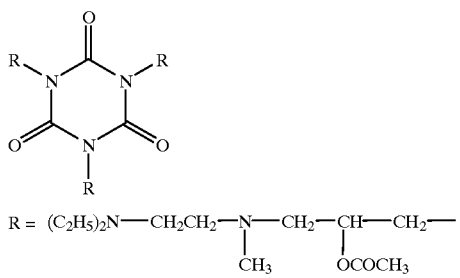

A-42

R = (C₂H₅)₂N—CH₂CH₂—N—CH₂—CH—CH₂—
              |            |
              CH₃         OCOCH₃

Suitable contrast-boosting phosphonium compounds are described, for example, by general formula (P)

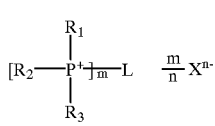

(P)

wherein

R₁, R₂ and R₃ each represent an alkyl, cycloalkyl, aryl, alkenyl or cycloalkenyl group or a heterocyclic group, wherein these groups may each also have substituents, L represents an m-valent organic group bound to the phosphorus atom via a carbon atom, n represents 1, 2 or 3, x represents an n-valent anion which may also be bound to L.

Examples of suitable phosphonium compounds include

P-1

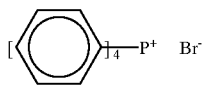

P-2

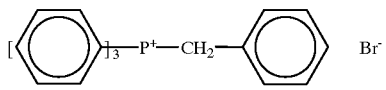

P-3

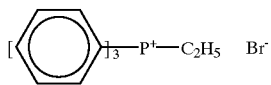

P-4

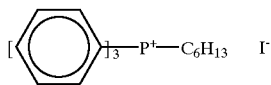

P-5

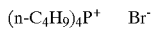

(n-C₄H₉)₄P⁺  Br⁻

P-6

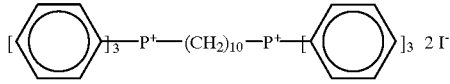

P-7

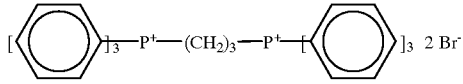

P-8

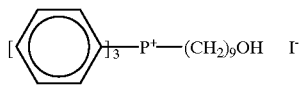

P-9

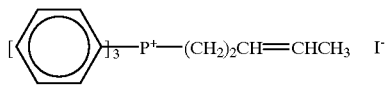

P-10

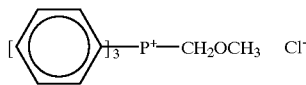

P-11

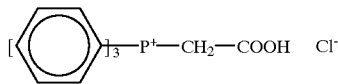

P-12

(n-C₄H₉)₃—P⁺—(n-C₁₆H₃₃)  Br⁻

P-13

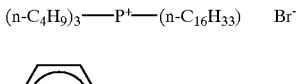

P-14

P-15

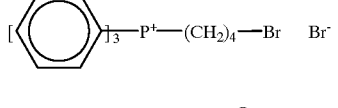

The light-sensitive silver halides in the recording materials used according to the invention consist of silver chloride, silver bromide, silver chlorobromide, silver bromoiodide or silver chlorobromoiodide, silver bromide and silver bromoiodide being preferred. They may be monodisperse or polydisperse, have a uniform composition or also contain grains with a core and shell structure, as well as mixtures of grains having different compositions and grain size distributions. They are produced using a hydrophilic colloidal binder, preferably gelatin. The silver halide grains may have a spherical, polyhedric or platy configuration. A person skilled in the art is familiar with methods of producing suitable light-sensitive silver halide emulsions which are summarised, for example, in Research Disclosure 365 044, Chapters I to IV (September 1994).

Silver halide emulsions which are produced by controlled double-beam influx and have a cubic grain shape are preferred for the recording materials used according to the invention. Emulsions in which at least 80% by weight of the silver halide is in cubic form are advantageous. Monodisperse emulsions, i.e. those in which the variation coefficient (quotient of standard deviation and mean value) of the grain size is smaller than 0.30 are particularly preferred. The term grain size denotes the edge length of a cube having the same volume as the actual grain.

The grain volume of the silver halide grains in the emulsions is based on the required speed and may correspond, for example, to a cubic grain having an edge length of 0.1 to 0.7 μm. A preferred range lies between 0.15 and 0.30 μm. Salts of precious metals, in particular salts of rhodium or iridium, may be present in the normal quantities to control the photographic properties during production of the emulsions.

The emulsions are preferably chemically sensitised. Suitable processes include sulphur, reduction and precious metal sensitisation, which may also be combined. Gold or iridium compounds, for example, may be used for precious metal sensitisation. Sensitisation is preferably carried out in the presence of salts of organic thiosulphonic acids such as p-toluene thiosulphonic acid.

The emulsions may be spectrally sensitised with conventional sensitisation dyes, as described, for example, in Research Disclosure 365 044, Chapter V (September 1994). Sensitisers for red (wavelength 600 . . . 690 nm) and infrared (>690 nm) light are preferred.

The emulsions may also contain conventional antifogging agents. Optionally substituted benzotriazole, 5-nitroindazole and 1-phenyl-5-mecaptotetrazole are preferred. These agents may be added at any time during production of the emulsions or may be contained in an auxiliary layer of the photographic material.

An iodide, preferably an alkali iodide, may be added to the emulsion before or after chemical ripening, in a quantity of about 0.5 to 5 millimoles per mole of silver to improve the photographic properties.

The emulsions may also contain known polymer dispersions by means of which, for example, the dimensional stability of the photographic material is improved. These are generally latices of hydrophobic polymers in an aqueous matrix. Examples of suitable polymer dispersions are mentioned in Research Disclosure 176 043, Chapter IX B (December 1978). Polymers of acrylic and methacrylic acid esters are preferred, $C_1$ to $C_6$-esters being particularly preferred. The particle size of these polymer latices is preferably between 20 and 100 nm.

The layers of the photographic materials may be cured by addition of a curing agent. Curing agents are mentioned, for example, in Research Disclosure 365 044, Chapter II B (September 1994). This curing agent may be added to the emulsion or introduced via an auxiliary layer, for example a protective outer layer. Suitable curing agents include, for example, aldehydes such as formaldehyde or glutaraldehyde, vinyl sulphones, s-triazines, aziridines, carbodiimides, carbamoylpyridinium compounds, mono- and difunctional carbamoylimidazolium compounds. Hydroxydichlorotriazine is a preferred curing agent.

The photographic material may contain further additives which are known and conventional for producing specific properties. These agents are mentioned in the Research Disclosure 365 044 (September 1994) in Chapers VI (brighteners), IX A (coating auxiliaries), IX B (plasticisers and lubricants) and IX D (delustring agents).

The gelatin content of the emulsions is generally between 30 and 150 g per mole of silver. The range is preferably between 40 and 100 g per mole of silver.

The silver halide materials according to the invention may be used for producing black and white negatives with ultrahard-gradation contrast. They may be exposed imagewise with a suitable light source for this purpose. This may be effected all over using a master, for example with an incandescent lamp or a discharge lamp, optionally by means of a colour filter, or alternatively by scanning with an intensity-modulated light beam, for example from a gas, solid or semiconductor laser. A preferred process employs a HeNe laser or a semiconductor laser with emission in the red range of the spectrum.

Processing of the exposed material to produce the image preferably involves treatment with an aqueous development bath, with an aqueous fixing bath, washing and drying.

Processing is preferably carried out as a high speed process with a development time of at most 30 s and appropriately adapted developer temperature, for example 32° C. and higher. To attain a high speed of development and to minimize the quantity of waste solution by a low regeneration rate, it is preferable to use developer solutions with a high content of developer substance, for example more than 25 g per liter.

The developer solutions preferably contain a dihydroxybenzene developer substance, for example hydroquinone, catechol, methyl hydroquinone or chlorohydroquinone, and an antioxidant, preferably an alkali sulphite in a concentration higher than 0.3 moles per liter. Solutions with pH values of 9 to at most 11 are preferably used, and those with pH values of 10 to 10.5 particularly preferably used. These developer solutions are also stable in use. Developer solutions with a developer substance of the ascorbic acid type, for example L-ascorbic acid, D-ascorbic acid, L-erythroascorbic acid, 6-desoxy-L-ascorbic acid, imino-L-erythroascorbic acid or sugar derivatives of these acids may also be used. Developer solutions which contain developer substances of the dihydroxybenzene type as well as those of the ascorbic acid type are also suitable.

The developer solutions preferably contain known auxiliary developer substances which have a superadditive effect, for example N-methyl-p-aminophenol or 1-phenylpyrazolidinone-3 or derivatives of these compounds.

Developers containing anti-fogging agents from the benzotriazole group are also preferred. These anti-fogging agents include, for example, benzotriazole, 5-chlorobenzotriazole, 5-bromobenzotriazole, 5-methylbenzotriazole, 5-nitrobenzotriazole, 5-benzoylaminobenzotriazole, 1-hydroxymethylbenzotriazole, 6-cyanobenzotriazole.

The recording materials according to the invention are distinguished not only by excellent stability in storage. They are also faster and exhibit higher contrast values. If higher speed is not required, it is possible to use a smaller amount of sensitiser dye and thus to obtain materials without undesirable coloration due to dye residues after processing. However, it is also possible to use finer grained silver halide and to manage with a smaller application of silver halide, owing to the higher covering capacity of the silver developed from it.

The invention may be used for producing black and white negatives with ultrahard-gradation contrast, in particular during reproduction in the pre-printing stage for black and white and multi-coloured printing.

The quantities of emulsion additives in the following embodiment relate to one mole of silver halide, unless otherwise stated.

EXAMPLE 1

A cubic silver bromoiodide emulsion (2 mole % of iodide) having grains with an edge length of 0.18 μm was produced by pAg controlled double beam precipitation in an aqueous gelatin solution. After removal of the soluble salts by flocculation, redispersion was carried out using further gelatins and chemical ripening using 0.01 millimoles of hexachloroplatinic acid, 8 mg of potassium thiotosylate, 6 mg of benzene sulphinic acid, 0.4 millimoles of thiosulphate and 0.1 millimoles of tetrachloroauric acid. A further 5 millimoles of potassium iodide, 300 mg of 7-hydroxy-1-methyltriazaindoline, 200 mg of 5-nitroindazole, a sensitiser for the red range of the spectrum, a coating auxiliary (Triton® X-200; manufactured by Rohm & Haas), 0.15 millimoles of 1-pyridiniumacetyl-2-(4-benzyloxyphenyl)hydrazinebromide (compound H-9), 600 mg of N-((3-dibutylaminopropyl)benzenesulphonamide hydrochloride (compound A-37) and 600 mg of polyvinyl pyrrolidinone (molar mass 30000) as well as stabilising compounds according to Table 1 were added.

Scanner films were produced by application of the emulsion together with two gelatin-containing protective coating solutions to a polyethylene terephthalate substrate provided with an antistatic and anticurl backing. 3.5 g per $m^2$ of silver were applied and the protective layers contained, per $m^2$, a total of 0.9 g of gelatins, 500 mg of colloidal silica as well as polyethylene oxide 4000, hydroquinone and a polyolefin oxidate according to DE 43 11 888. The coating was cured by addition of 0.1 millimoles of hydroxydichlorotriazine, and bis-dimethylcarbamoylimidazolium chloride, per gram of gelatin in each case, to the coating solutions.

Samples of the recording materials obtained were exposed with a flashlight (exposure time $10^{-3}$ s) through a red filter and a density gradient profile and were processed with a developer having the composition specified hereinafter as well as a conventional commercial fixing bath in an automatic development machine.

Development took place at 35° C. and lasted 30 s. A conventional commercial fixing bath was used. Speed S as turning value of exposure with respect to 100 in the case of sample 1, contrast G1 between the density values 0.1 and 0.4, contrast G2 between the 0.4 and 3.5, fog Dmin and maximum density Dmax were determined on the processed samples. The films were stored at 22° C. and 55% relative humidity and were tested 3 days and 3 months after production. The results are shown in Table 1.

| Composition of the developer (all components in g) | |
| --- | --- |
| Water | 500 |
| Sodium bisulphite | 50 |
| Potassium hydroxide | 27 |
| Ethylene diamine tetraacetic acid, trisodium salt | 3.7 |
| Hydroquinone | 25 |
| Potassium bromide | 4 |
| Benzotriazole | 0.3 |
| Phenylmercaptotetrazole | 0.05 |
| 4-hydroxymethyl-4-methyyl-1-phenylpyrazolidinone | 1 |
| Boric acid | 3 |
| Sodium hydroxide | 24 |
| Diethylene glycol | 40 |
| Fill to 1 liter with water, adjust pH to 10.5 at 22° C. | |

TABLE 1

| | Stabiliser | | | | | | |
| --- | --- | --- | --- | --- | --- | --- | --- |
| Sample | comp. | quant. (mg) | Dmin | Dmax | S | G1 | G2 |
| 1 | none | additive | 0.04 (0.06) | 6.5 (6.5) | 100 (100) | 2.5 (2.0) | 15 (13) |
| 2 | PMT | 40 | 0.04 (0.06) | 6.0 (6.0) | 50 (50) | 2.5 (2.2) | 10 (10) |
| 3 | BT | 80 | 0.04 (0.05) | 6.3 (6.3) | 79 (71) | 2.4 (2.3) | 13 (12) |
| 4 | BT | 160 | 0.04 (0.05) | 6.3 (6.3) | 66 (63) | 2.1 (2.0) | 10 (9) |
| 5 | $Na_2SO_3$ | 20 | 0.04 (0.05) | 6.5 (6.5) | 100 (100) | 2.6 (2.2) | 15 (13) |
| 6 | $Na_2SO_3$ | 200 | 0.04 (0.04) | 6.5 (6.5) | 117 (117) | 4.3 (4.1) | 17 (16) |
| 7 | $Na_2SO_3$ | 400 | 0.04 (0.04) | 6.5 (6.5) | 126 (126) | 5.0 (5.0) | 19 (19) |
| 8 | $Na_2SO_3$ | 800 | 0.04 (0.04) | 6.5 (6.5) | 126 (126) | 5.2 (5.0) | 21 (21) |
| 9 | $Na_2S_2O_5$ | 400 | 0.04 (0.04) | 6.5 (6.5) | 126 (126) | 5.0 (5.0) | 19 (19) |

PMT = phenylmercaptotetrazole,
BT = benzotriazole,

The values measured after three months are shown in brackets beneath the three-day values.

EXAMPLE 2

Red-sensitive recording materials have been produced in the same way as in Example 1. However, 0.06 moles of the phosphonium compound P-1 have been used instead of the amino compound A-37 and polyethylene oxide 20000 has been used instead of polyethylene oxide 4000. A sulphite salt has also been added, as mentioned in Table 2.

The materials were examined and evaluated as described in Example 1. The results are compiled in Table 2, in the same way as in Table 1.

| | Stabiliser | | | | | | |
| --- | --- | --- | --- | --- | --- | --- | --- |
| Sample | comp. | quant. (mg) | Dmin | Dmax | S | G1 | G2 |
| 11 | none | additive | 0.04 (0.06) | 6.3 (6.3) | 100 (100) | 2.7 (2.4) | 15 (12) |
| 12 | $Na_2SO_3$ | 400 | 0.04 (0.04) | 6.5 (6.5) | 141 (135) | 8.0 (7.5) | 22 (20) |

It has also surprisingly been found during this experiment that the increase in fog during storage is inhibited by addition of the sulphite salt, without speed or contrast being reduced. The contrast is also significantly increased, in particular in the foot region.

We claim:

1. Photographic silver halide material for producing black and white negatives comprising at least one light-sensitive silver halide emulsion layer on a substrate, the silver halide emulsion layer or a layer in a reactive relationship therewith containing a hydrazine compound and a contrast-boosting amino compound and/or phosphonium compound, and the silver halide emulsion layer or in a layer in a reactive relationship therewith, also contains a sulphite, hydrogen sulphite or bisulphite salt.

2. Material according to claim 1, wherein the sulphite, hydrogen sulphite or bisulphite salt is a salt of an alkali metal.

3. The material according to claim 2, wherein the quantity of sulphite, hydrogen sulphite or bisulphite salt is calculated so that it corresponds to 0.1 to 10 millimoles of sulphite ions per mole of silver halide.

4. Material according to claim 1 wherein the quantity of sulphite, hydrogen sulphite or bisulphite salt is calculated so that it corresponds to 0.05 to 20 millimoles of sulphite ions per mole of silver halide.

5. Material according to claim 1, wherein the hydrazine compound has the formula B-phenyl-NHNH—L—G wherein B is a ballest group, G an activating group, and -phenyl- an optionally substituted phenylene radical and L is CO or CO—CO.

6. The material according to claim 5, wherein the quantity of sulphite, hydrogen sulphite or bisulphite salt is calculated so that it corresponds to 1 to 10 millimoles of sulphite ions per mole of silver halide.

7. The material according to claim 5, wherein the phenylene group to which B and the hydrazine group are bound in the para position.

8. Material according to claim 1, wherein the contrast-boosting amino compound is of the formula (A)

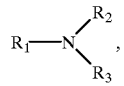
(A)

wherein each of the substituents $R_1$, $R_2$ and $R_3$ are identical or different and are a hydrogen atom, an alkyl group, a substituted alkyl group, an alkenyl group, a substituted alkenyl group, an alkinyl group, an aryl group or a substituted aryl group, the substituents may be linked to form one or two rings, but $R_1$, $R_2$ and $R_3$ are not all simultaneously hydrogen.

9. Material according to claim 1, wherein the contrast-boosting amino compound is of the formulae $RR^1N$—X—$(CN)_n$ (B)

NC—X—$NR^2$—B—$NR^2$—X—CN (C)

$RR^1N$—X—$N(CH_2CN)_2$ (D)

wherein

R and $R^1$, which may be the same or different, each represent an optionally substituted alkyl group containing 1 to 6 carbon atoms or an optionally substituted benzyl group, or R and $R^1$ together with the nitrogen atom and optionally a further oxygen or nitrogen atom, represent a five- to eight-membered ring, $R^2$ represents a saturated or unsaturated alkyl group or an aryl group, these groups may be further substituted, moreover an alkyl group may be bound by its end remote from the nitrogen to a carbon atom from group B to form a ring, x represents a divalent or trivalent combining group, B represents a divalent combining group, n is 1 or 2.

10. The material according to claim 9, wherein $R_2$ is a saturated or unsaturated alkyl group containing 1 to 12 carbon atoms, an aryl group containing 6 to 14 carbon atoms or an aralkyl group containing 7 to 15 carbon atoms, which in turn these groups may be substituted with a substituent selected from the group consisting of hydroxyl, amino, alkylamino, alkoxy and alkyl containing one to six carbon atoms.

11. Material according to claim 1, wherein the silver halide emulsion is a silver bromide or silver iodobromide emulsion.

12. Material according to claim 1, wherein the silver halide emulsion is sensitized to red and/or infrared light.

13. A process for producing black and white negatives with ultrahard-gradation contrast which comprises exposing the material according to claim 1.

14. Material according to claim 1 wherein the phosphonium compound has the formula (P)

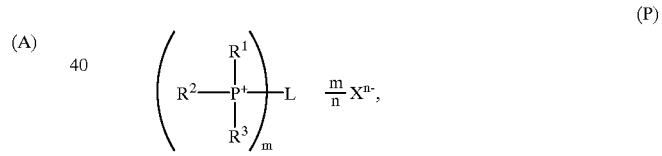
(P)

wherein $R_1$, $R_2$ and $R_3$ are identical or different and are an alkyl, cycloalkyl, aryl, alkenyl or cycloalkenyl group or a heterocyclic group, wherein these groups may each also have a substituent, L represents an m-valent organic group bond to the phosphorus atom via a carbon atom, n represents 1, 2 or 3, X represents an n-valent anion which may also be bound to L.

* * * * *